United States Patent [19]

Ludwig

[11] Patent Number: 5,391,271
[45] Date of Patent: Feb. 21, 1995

[54] METHOD OF MONITORING ACID CONCENTRATION IN PLATING BATHS

[75] Inventor: Frank A. Ludwig, Rancho Palos Verdes, Calif.

[73] Assignee: Hughes Aircraft Company, Los Angeles, Calif.

[21] Appl. No.: 127,018

[22] Filed: Sep. 27, 1993

[51] Int. Cl.⁶ .............................................. G01N 27/26
[52] U.S. Cl. .................................. 204/153.1; 204/434
[58] Field of Search ............................... 204/153.1, 434

[56] References Cited

U.S. PATENT DOCUMENTS 4,631,116 12/1986 Ludwig ................................ 204/434

Primary Examiner—John Niebling
Assistant Examiner—Bruce F. Bell
Attorney, Agent, or Firm—M. E. Lachman; M. W. Sales; W. K. Denson-Low

[57] ABSTRACT

A method of monitoring the concentration of certain plating bath major constituents such as acid is provided which is insensitive to the effects of hydrogen produced during plating. The method involves applying an ac signal superimposed on a dc potential to a sensing electrode in contact with the solution, producing an ac response current. The steady state value of the ac response current is then measured and provides an accurate indication of the acid concentration within the solution. The method can be performed using a single sensing electrode. Furthermore, the method complements and is easily integrated with known voltammetric techniques and equipment suitable for analysis of other plating bath constituents.

11 Claims, 1 Drawing Sheet

METHOD OF MONITORING ACID CONCENTRATION IN PLATING BATHS

This invention was made with support provided by the United States Government under Contract Number DAAB07-88-A047 awarded by the Department of the Army. The U.S. Government has certain rights in this invention.

BACKGROUND OF THE INVENTION

1. Field of the Invention

The present invention relates generally to plating baths and methods for monitoring the constituents contained therein. More particularly, the method of the present invention relates to a voltammetric analysis technique for monitoring the concentration levels of certain plating bath major constituents such as acid. The method can be used to maintain desired constituent concentrations in order to ensure optimal plating bath performance.

2. Description of Related Art

A typical plating bath solution is comprised of a combination of several distinct electrochemical constituents which can be broadly divided into major constituents and trace constituents. The major constituents typically make up about 2 to 50 percent of the total bath weight or volume. Trace constituents are present in smaller quantities, usually less than 1 percent of the total weight or volume. Acid is an important major constituent in many plating baths. For example, in an acid cadmium plating bath, acid typically represents about 5 to 10 percent of the total bath weight.

The concentration levels of both major and trace constituents will influence the quality of the resultant plating deposit, and should therefore be regularly monitored. Methods have been developed for in-tank monitoring of trace constituents as well as certain major constituents. For example, U.S. Pat. No. 4,631,116 discloses a method for monitoring trace constituents using an in-tank electrochemical sensor. Application Ser. No. 08/037,158 entitled "Method of Monitoring Major Constituents in Plating Baths" discloses a method for in-tank monitoring of major constituents such as sulfuric acid in an acid copper bath. The above patent and pending patent application are owned by the same assignee as the present invention. However, these techniques provide less than optimal accuracy for certain types of acid, particularly in plating baths in which large quantities of hydrogen are produced during plating. For example, the above voltammetric techniques are not well-suited to measurement of acid in an acid cadmium bath. As a result, alternative techniques are currently used to measure acid cadmium concentrations.

One such technique involves the use of two sensors; one voltammetric, the other a conductivity sensor. The two sensors are required because often voltammetric sensors measure non-acid constituents, whereas conductivity relates to acid concentration. Other techniques currently used to measure relatively high acid concentrations in plating baths which produce large amounts of hydrogen during plating include pH sensors which are not very accurate at high acid concentrations. Use of the current measurement techniques is inconvenient, time-consuming and costly, since these techniques are not directly compatible with the voltammetric trace and major constituent measurement methods discussed above. Additional tests must be performed using a different set of equipment in order to properly monitor certain acid concentrations. No integrated measurement system is available which is capable of measuring these acid concentrations as well as most other major and trace constituent concentrations.

As is apparent from the above, there presently is a need for an accurate and inexpensive real time method of monitoring acid concentrations in plating baths which produce large quantities of hydrogen. The method should require the use of only a single in-tank sensor. Furthermore, the method should complement and be easily integrated with known techniques and equipment suitable for measuring other plating bath constituents, resulting in an efficient overall plating bath analysis system.

SUMMARY OF THE INVENTION

The present invention provides a method for monitoring the concentration of acid as a plating bath major constituent. The present invention is based upon the discovery that the concentrations of certain major constituents such as acid can be accurately determined by measuring the steady state value of the ac response current produced when an ac signal superimposed on a dc signal is applied to a sensing electrode in contact with the solution.

The method of the present invention involves the steps of providing at least one sensing electrode in contact with a plating bath solution containing a concentration of acid or other major constituent; applying a voltammetric signal comprising an ac signal superimposed on a dc signal to the sensing electrode such that an ac response current is produced having a steady state value proportional to the constituent concentration; and measuring the steady state value of the response current to determine the constituent concentration.

As a feature of the present invention, the method is insensitive to the hydrogen produced during plating and is therefore well-suited to acid concentration measurements in plating baths which produce large amounts of hydrogen. The method can also be used to monitor acid concentrations in other types of plating baths.

As another feature of the present invention, the measurements may be performed using a single in-tank electrochemical sensor. The measurement results are available in real time so that desired major constituent levels, and thereby the quality of the plating bath, can be continuously and efficiently maintained.

As a further feature of the present invention, the method is easily integrated with known trace constituent measurement methods and equipment, thereby providing an efficient and flexible overall plating bath analysis system suitable for accurately monitoring a wide variety of plating baths and their respective constituents. Since the present invention can be implemented using voltammetric equipment suitable for measuring most other plating bath constituents, only a single set of equipment need be maintained. The method of the present invention thus serves to complement and extend the capabilities of existing voltammetric analysis techniques.

As an additional feature of the present invention, optimal signal parameters for monitoring acid concentration in an exemplary acid cadmium bath are disclosed. Furthermore, the method provides an experimental framework for determining optimal measurement signal parameters for monitoring acid or other major constituent concentrations in a wide variety of different plating baths.

The above-discussed features and attendant advantages of the present invention will become better understood by reference to the following detailed description of the invention and the accompanying drawings.

DESCRIPTION OF THE PREFERRED EMBODIMENT

The present invention has wide application to many different plating baths and their respective constituents. The following description is directed towards measurement of acid concentration, and applies the method to measuring acid concentration in an exemplary acid cadmium bath. It should be understood, however, that this is by way of example and not limitation. The method can be used to measure acid concentrations in most plating baths, including, for example, acid copper. Furthermore, although the method is particularly well-suited to the detection of acid concentrations as described herein, it could also be used to monitor a variety of other plating bath constituents. Other constituents which could be measured using this method include hydroxide ion.

Figure 1:
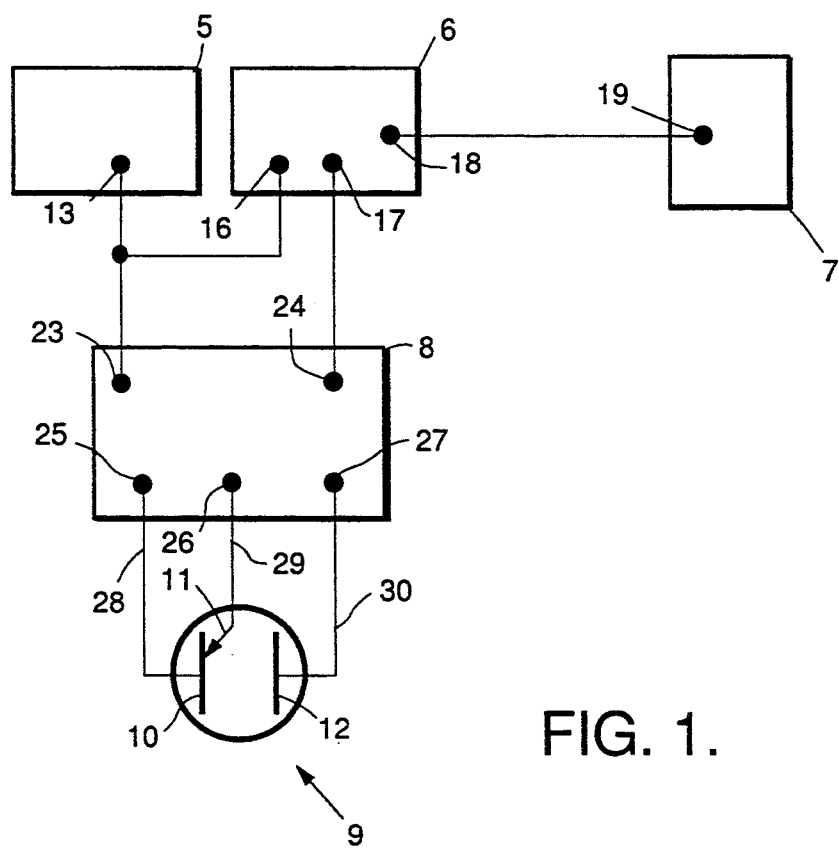
FIG. 1 is a schematic representation of a preferred exemplary system for conducting the method of the present invention.

The schematic diagram of FIG. 1 illustrates a preferred exemplary system for conducting the method of the present invention. It should be noted that the equipment of this system is readily compatible with the equipment used in conjunction with other voltammetric plating bath monitoring techniques. The present method therefore serves to extend the capability of existing voltammetric techniques without the need for additional equipment.

In the exemplary system of FIG. 1, the plating bath solution is located within an electrochemical cell 9. The electrochemical cell 9 is preferably part of an in-tank electrochemical sensor submerged within the plating bath. A pump (not shown) can be used to draw the solution through cell 9. Waveform generator 5 provides an output 13 which is an ac signal of suitable waveform, amplitude and frequency. The ac signal is preferably a sinusoidal signal, but other ac waveforms could also be used, such as square waves. The ac signal is applied to the external input 23 of a potentiostat 8 and to the reference input 16 of a lock-in amplifier 6. The potentiostat 8 forms the desired voltammetric signal by superimposing the ac signal applied to its external input 23 upon an appropriate dc signal generated within the potentiostat. Alternatively, the dc signal could be supplied by an external signal source. The ac and dc signal characteristics will be discussed in greater detail below. Potentiostat 8 also ensures that signal amplitudes are not affected by variations in current flow through electrochemical cell 9. An exemplary potentiostat suitable for use in the system of FIG. 1 is the PAR model 273 available from Princeton Applied Research, of Princeton, N.J.

The voltammetric signal consisting of combined ac and dc signals is applied to the sensing electrode 10 in the electrochemical cell 9 via line 28. The sensing electrode is preferably constructed of an inert material such as platinum. The electrochemical cell 9 also contains a counter electrode 12 and a reference electrode 11. All system measurements are taken relative to the reference electrode 11. The reference electrode can be a standard calomel reference electrode or any other suitable reference electrode. The reference electrode 11 and counter electrode 12 are connected to the potentiostat 8 via lines 29, 30 respectively. This three-electrode electrochemical sensor design is suitable for use with many different voltammetric techniques. Further detail on this sensor can be found in U.S. application Ser. No. 07/945,751 entitled "In-tank Electrochemical Sensor," assigned to the present assignee. It should be understood, however, that alternative electrode arrangements may also be used.

When the combined dc and ac signal is applied to sensing electrode 10, a response current is generated between sensing electrode 10 and counter electrode 12. The response current has an ac component and a dc component.

The response current is measured in the following manner. The response current passes back through potentiostat 8 from output 24 to the signal input 17 of lock-in amplifier 6. The lock-in amplifier separates the ac component of the response current from the dc component. A reference signal is supplied from the voltammetric ac signal source, waveform generator 5, to the reference input 16 of lock-in amplifier 6. The reference is coherent with the ac component of the response current signal and lock-in amplifier 6 can then be used to measure the ac response current. Alternatively, the output 18 of lock-in amplifier 6 can be applied to input 19 of a digital voltmeter 7 set to measure ac millivolts. In another possible embodiment, the lock-in amplifier could be eliminated altogether and input 19 of voltmeter 7 could be connected directly to output 24 of potentiostat 8. When the voltmeter is set to measure ac millivolts it will be unaffected by the dc component of the response current. Other suitable methods of measuring ac voltage could be used in place of voltmeter 7.

In order to optimize the response current accuracy as an indicator of a particular acid concentration, the ac signal waveform, amplitude and frequency and the dc signal amplitude and duration can be varied. These parameters were independently varied to determine the preferred system parameters for monitoring acid concentration using the preferred voltammetric system of FIG. 1. It should be noted, however, that alternative combinations of ac and dc signal parameters may also produce similar measurement results.

In general, certain system parameters are particularly well-suited for selectively monitoring particular acid concentrations. The preferred signal characteristics for the ac and dc components of the voltammetric signal are as follows. All potentials and voltages are given with respect to a saturated calomel electrode. The ac signal preferably has an amplitude of about 10 to 200 mv rms and a frequency of about 5 to 60 kH. The high frequency eliminates the effect of the electrode reactions and responds mainly to solution conductivity. The method of the present invention is thus able to isolate the effect of the acid from that of the other plating bath constituents due to the high conductivity of acid. For example, in the case of an acid cadmium plating bath, the cadmium ions are much less conductive. However, the high proton conduction in most acids permits the acid to respond to the ac component of the voltammetric signal. The ac response current is therefore primarily a function of the acid concentration within the bath.

The dc signal is set at an anodic potential of about 2.0 to 3.5 volts applied for a period of about 5 to 15 seconds. This dc signal is similar to the anodic pretreatment signals described in U.S. Pat. No. 4,631,116 and application Ser. No. 08/037,158. The dc component of the preferred voltammetric signal of the present invention thus also provides the cleaning and activation functions of a pretreatment signal. The dc signal removes any absorbed organics or other contaminants from the sensing electrode surface and otherwise prepares it for measurements of ac response current. The sensitivity of the method is insensitive to the degree of stirring or agitation of the plating bath solution.

The steady state magnitude of the ac component of the response current generated and measured as described above provides an accurate indication of acid concentration. The ac current should be given sufficient time to reach a steady state value before it is measured. In general, the ac response current will reach steady state in about 3 to 10 seconds. For purposes of this specification, the response current is considered to have reached steady state when it consistently maintains about ± one percent of its final value. Other ac wave forms could also be used to indicate acid concentration, including triangular or square wave.

The voltammetric system of FIG. 1 has been applied to the detection of acid concentration in an exemplary acid cadmium plating bath available from LeaRoanal of Freeport, N.Y. The acid was a major constituent within this exemplary acid cadmium bath, at a concentration level of about 5–10 percent of total bath weight. Cadmium ions comprised the other major constituent within the bath, present in a concentration of about 3–5 percent of total bath weight. The acid cadmium bath typically produces large amounts of hydrogen during plating.

The ac component of the voltammetric signal applied to this exemplary solution was a sinusoidal signal having an amplitude of about 10 to 100 mv rms and a frequency of about 30 to 55 kHz. The ac component was superimposed on a dc signal set at an anodic potential of 3.0 volts. The magnitude of the ac component of the response current reached its steady state value after this voltammetric signal had been applied for 5 seconds. The steady state ac response current was then measured for various acid concentrations. The results of these measurements are summarized in Table 1 below. The sensing electrode was a 1 mm diameter platinum wire sheathed at both ends, so that only a ⅛ inch long cylindrical surface was exposed to the plating solution.

TABLE I

| Steady state ac response current at various normalized acid concentrations | |
|---|---|
| Acid Concentration | Steady State Current (ma) |
| 1.0 | 12.1 |
| 0.8 | 10.6 |
| 1.2 | 13.3 |

The above measurement results are normalized to a value of 1.0, which corresponds to an acid concentration of about 75 grams/liter. The steady state ac response current of 12.1 ma corresponding to this acid concentration is plotted as point P1 in FIG. 2. Decreasing the acid concentration to a normalized value of about 0.8 results in an ac response current of about 10.6 ma. This measurement is plotted as point P2 in FIG. 2. Increasing the acid concentration to a normalized value of 1.2 results in an ac response current of 13.3 ma, as shown by point P3 in FIG. 2.

Figure 2:
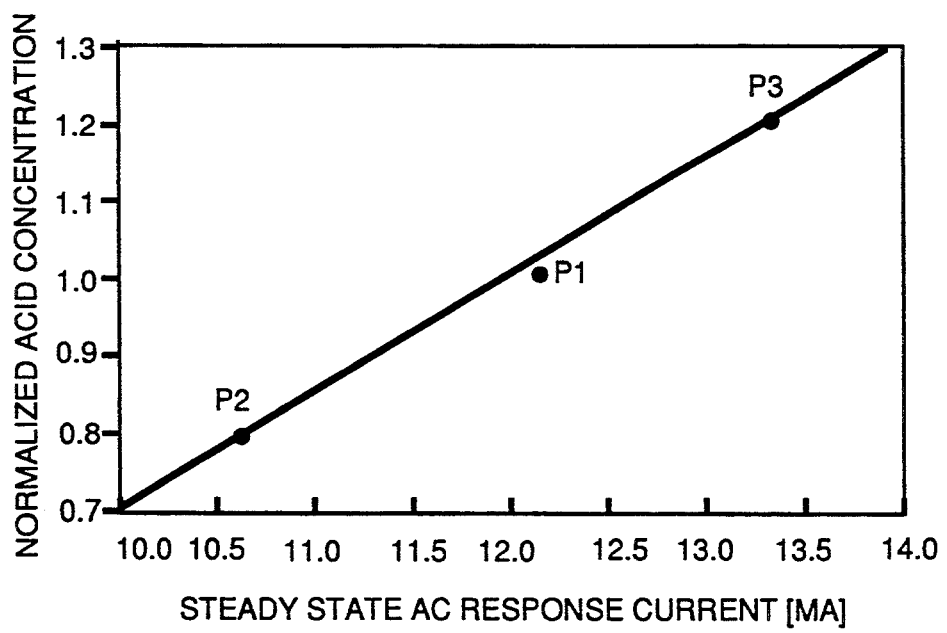
FIG. 2 is a graph of the steady state ac response current as a function of acid concentration in an exemplary acid cadmium plating bath.

It can be seen from FIG. 2 that the steady state ac response current is a linear function of acid concentration. The maximum total error or deviation from linear for a given measurement point is about 3 percent. The above measurements are also relatively insensitive to the concentration levels of other major constituents within the plating bath. For example, increasing the cadmium ion content by 20% had no effect on the acid concentration measurements.

Although the above detailed description is directed to detecting acid concentrations in plating baths which generate large amounts of hydrogen during plating, this is by way of example and not limitation. The method can also be used to monitor major constituents other than acid, such as hydroxide ion. Furthermore, the method can be applied to plating baths which do not generate large quantities of hydrogen during plating. It will be understood by those skilled in the art that these and many other alternate implementations are possible without deviating from the scope of the invention, which is limited only by the appended claims.

The contents of the patents and copending patent applications set forth above are hereby incorporated by reference.

What is claimed is:

1. A method of monitoring a concentration of a major constituent within a plating bath solution, said method comprising the steps of:
   providing at least one sensing electrode in contact with said solution;
   applying a voltammetric signal to said sensing electrode, said voltammetric signal comprising an ac signal having an amplitude of about 10 to 200 mv rms and a frequency of about 5 to 60 kHz superimposed on a dc signal set at an anodic potential within the range of about 2.0 to 3.5 volts and having a duration of about 5 to 15 seconds, said voltammetric signal producing an ac response current having a steady state value proportional to said concentration of said major constituent; and
   measuring said steady state value of said response signal current to determine said concentration of said major constituent.

2. The method of claim 1 wherein said major constituent in said plating bath solution is acid.

3. The method of claim 2 wherein said concentration of said acid comprises about 2 to 50 percent of the total weight of said plating bath solution.

4. The method of claim 1 wherein said voltammetric signal is applied to a single sensing electrode.

5. The method of claim 1 wherein said ac signal is a sinusoidal ac signal.

6. The method of claim 1 wherein said plating bath solution is an acid cadmium plating bath solution.

7. The method of claim 6 wherein said ac signal is a sinusoidal ac signal.

8. The method of claim 6 wherein said ac signal has an amplitude of about 25 mv rms.

9. The method of claim 6 wherein said ac signal has a frequency of about 30 to 55 kHz.

10. The method of claim 6 wherein said dc signal is an anodic potential of about 3.0 volts.

11. The method of claim 6 wherein said dc signal has a duration of about 5 seconds.

* * * * *